F. RIGHTMIRE.

DEVICE FOR TREATING CUTANEOUS DISEASES.

APPLICATION FILED MAR. 19, 1910.

Reissued Aug. 19, 1913. 13,608.

WITNESSES:

Wm. D. Bell.

Elsie Kaufmann.

INVENTOR,

Franklin Rightmire,

BY

John Newland

ATTORNEY.

COLUMBIA PLANOGRAPH CO., WASHINGTON, D. C.

UNITED STATES PATENT OFFICE.

FRANKLIN RIGHTMIRE, OF PATERSON, NEW JERSEY.

DEVICE FOR TREATING CUTANEOUS DISEASES.

13,608. Specification of Reissued Letters Patent. Reissued Aug. 19, 1913.

Original No. 943,894, dated December 21, 1909, Serial No. 279,610. Application for reissue filed March 19, 1910. Serial No. 550,531.

*To all whom it may concern:*

Be it known that I, FRANKLIN RIGHTMIRE, a citizen of the United States, residing at Paterson, county of Passaic, and State of New Jersey, have invented certain new and useful Improvements in Devices for Treating Cutaneous Diseases; and I do hereby declare the following to be a full, clear, and exact description of the invention, such as will enable others skilled in the art to which it appertains to make and use the same, reference being had to the accompanying drawing, and to letters of reference marked thereon, which forms a part of this specification.

This invention relates to appliances for the treatment of diseases of the skin, such as corns, warts, bunions, and the like, and it has reference particularly to devices of this kind adapted to retain in contact with the affected part a medicinal or other agent whose function it is to afford relief or cure.

The object of the invention is to provide a device of the character referred to which will efficiently hold in place the agent to be retained thereby, may be readily applied to and removed from the affected part with as little irritation of the same in doing so as is possible, will, instead of producing discomfort or irritation by transmitting pressure or friction induced by the shoe or the like, relieve the part of such pressure, friction or other irritating influences, will be durable in construction, and may be manufactured at the minimum of cost.

Other objects will appear hereinafter or be apparent to those skilled in the art or having occasion to use devices of the character above indicated.

Figure 1:
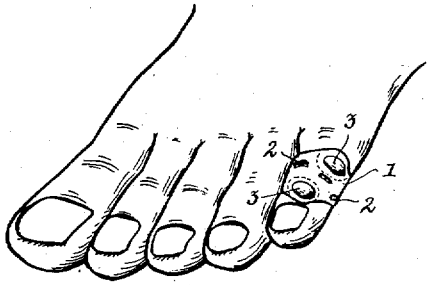
Figure 2:
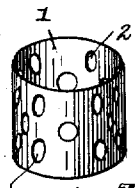
Figure 3:
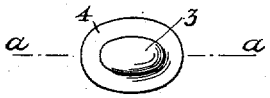

The invention is fully illustrated in the accompanying drawing, wherein,

Figure 1 shows one adaptation of my invention, to wit, the treatment of a corn or corns on the foot, a portion of a foot with the device in position on one toe thereof being shown in perspective; Fig. 2 shows in perspective the body-portion of the device; Fig. 3 is a plan of the cup-portion; and, Fig. 4 is a longitudinal sectional view on line *a—a* of Fig. 3.

In said drawing, the body-portion of the device, shown in Fig. 2 and marked 1, is formed of a piece of thin elastic rubber, preferably tubular; 2 designates a hole or holes formed in the same, being irregularly distributed, if three or more in number.

Figure 4:
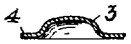

Figs. 3 and 4 show the cup-portion 3 of the device. Said cup-portion being, in the adaptation shown, separate from the body-portion, it has a continuous flange 4, projecting laterally from the mouth of the cup, the under surface of which in Fig. 4 is perfectly flat. Said cup-portion is likewise formed of elastic rubber, but it is less thin and less elastic than the material of the body-portion 1, the purposes of which will appear later on. When these parts, formed separate in the adaptation shown, are assembled, the cup-portion being introduced through one of the holes in the body-portion from the inside of the latter, and so that its flange 4 lies flat against the inside of the body-portion, a strap-like device is produced which is more elastic as to its body-portion 1 than as to its cup-portion 3, which latter projects from the outer surface of the body-portion and, while locked in the latter against outward displacement by its flange 4, does not produce an undue projection at the inner side of the body-portion.

Without regard to the feature involved in forming the device in separate parts, as in the adaptation shown for the purpose of illustration, the device possesses the following advantages, among others: its body-portion being of thin elastic rubber, it will fit closely around the affected part, lying approximately flush with the adjoining portions of the skin, so that its presence is not a source of discomfort to the wearer, however tightly a shoe or the like may be fitted to the affected part; for the same reason it is not calculated to become displaced or to roll or wrinkle under the friction induced by the shoe or other garment or in the movements of the affected part and, while it adheres closely to the skin and therefore serves to retain in the cup-member in strictly localized relation to the corn or the like which is being treated by the medicament which the cup is designed to contain, it may be readily stretched to have access to the diseased portion or to the cup. It is moreover freely flexible, so that it will not only adjust itself to a joint but not in the least embarrass the flexing action thereof. Its cup-portion, being also elastic and thin, but less so than its body-portion, said cup-portion yields somewhat to the pressure of a more or less tightly fitting garment, such as a shoe, so that, while it has sufficient stability to prevent such pressure from being imposed upon the sensitive spot of the diseased portion and to prevent the medicament being squeezed out of the cup, it will not exert undue pressure around the diseased portion or cause the corresponding part of the shoe or other tightly fitting garment to assume the form of a protuberance. Moreover, being thicker than the body-portion, it has a certain increased stability necessary for the convenient and facile introduction of the medicinal agent, such as absorbent cotton impregnated with a medicament, it being remarked that the formation of the device as a whole makes it possible in many instances to recharge the cup with the medicinal agent without the necessity of removing it from the affected part. Still again, because its walls are thicker than the body-portion of the device, it is better adapted to resist both the disintegrating influences of the medicament and such wear as a shoe or other tightly fitting garment would be likely to subject it to.

By forming the device in two separate portions, interlocked in the manner above described, the cup-portion may be removed for introducing the medicinal agent or removing it; this, moreover, without removing the body-portion from the affected part, if desired. The device is more durable, as when made in a single piece the cup-portion might become torn away from the body-portion, and it is more readily and cheaply manufactured. The flange augments the sealing-in of the medicinal agent within the cup and prevents absolutely the release of the cup-portion when the device is in place.

The two or more holes 2 shown in Figs. 1 and 2 have for their function to receive two or more of the cup-members and they are irregularly disposed so that the device may be adjusted to accommodate itself to any possible arrangements of the corns or other diseased parts.

Having thus fully described my invention, what I claim and desire to secure by Letters Patent is:

1. A device for the treatment of cutaneous diseases, comprising, in combination, a rubber strap-like member having substantially uniform thickness throughout and being in all parts thereof relatively thin and also elastic and having an opening therein and a cup-member having a flange projecting laterally from its mouth portion, said cup member being thin and elastic but less thin and less elastic than the first member, being received in the opening of the first member, and having its flange lying against one side, and its convex side projecting from the other side, of the first member, substantially as described.

2. In a device of the class described, in combination, a tubular section of elastic material having therein a plurality of openings, said tubular section being adapted to be positioned about a portion of the body, and a flanged cup adapted to be inserted underneath a portion of said elastic material so as to interlock with said elastic tubular section.

3. In a device of the class described, in combination, a section of rubber tubing having therein a plurality of irregularly arranged openings, said tubing being adapted to be positioned about a portion of the body, and a flanged, substantially cup-shaped member adapted to be inserted between a portion of the body and said tubing, the convex portion of said cup-shaped member entering one of the openings in said tubing, the edges of said opening being adapted to engage the flange upon said member to hold the same firmly in position upon the body.

In testimony that I claim the foregoing, I have hereunto set my hand this 16th day of March, 1910.

FRANKLIN RIGHTMIRE.

Witnesses:
JOHN W. STEWARD,
WM. D. BELL.

Copies of this patent may be obtained for five cents each, by addressing the "Commissioner of Patents, Washington, D. C."